(12) United States Patent
Lévesque

(10) Patent No.: US 6,339,071 B1
(45) Date of Patent: Jan. 15, 2002

(54) ANTISENSE OLIGONUCLEOTIDE MODULATING CYCLIN E GENE EXPRESSION AND THERAPEUTIC USES THEREOF

(75) Inventor: Luc Lévesque, Boucherville (CA)

(73) Assignee: Angiogène Inc., Montreal (CA)

( * ) Notice: Subject to any disclaimer, the term of this patent is extended or adjusted under 35 U.S.C. 154(b) by 0 days.

(21) Appl. No.: 09/488,074

(22) Filed: Jan. 20, 2000

Related U.S. Application Data

(60) Provisional application No. 60/140,446, filed on Jun. 23, 1999.

(51) Int. Cl.[7] .......................... A01N 43/04; C12Q 1/68; C12N 15/63; C07H 21/02; C07H 21/04
(52) U.S. Cl. .......................... 514/44; 435/6; 435/91.1; 435/455; 435/375; 536/23.1; 536/24.5
(58) Field of Search .................. 435/6, 91.1, 91.31, 435/455; 514/44; 536/25.3, 23.1, 24.5

(56) References Cited

U.S. PATENT DOCUMENTS

| | | | |
|---|---|---|---|
| 5,449,755 A | * | 9/1995 | Roberts et al. ............. 530/350 |
| 5,763,219 A | * | 6/1998 | Keyomarsi |
| 5,869,462 A | * | 2/1999 | Dzau ........................... 514/44 |

OTHER PUBLICATIONS

James, W. Antiviral Chem and Chemotherapy, vol. 2, No.4, pp. 191–214, 1991.*
Milner et al. Nature Biotech., vol. 15, pp. 537–541, 1997.*
Schofield et al. Brit. Med. Bull., vol. 51, No. 1, pp. 56–71, 1995.*
Friedmann, T. Scientific American, Jun. 1997 vol., pp. 96–101.*
Crystal, R.G. Science, vol. 270, pp. 404–410, 1995.*
Verma et al. Nature, vol. 389, pp. 239–242, 1997.*
Branch, A.D. Trends in Biochem. Sci. (TIBS), vol. 23, pp. 45–50, 1998.*
Jolly, D. Cancer Gene Therapy, vol. 1, No. 1, pp. 51–64, 1994.*
Crooke, S.T. Antisense Research and Application, Chapter 1, pp. 1–50. Published by Springer–Verlag, 1998.*
Orkin et al. Report and Recommendations of the Panel to Assess the NIH Investment in Research on Gene Therapy, 1995.*

* cited by examiner

*Primary Examiner*—Andrew Wang
*Assistant Examiner*—Jane Zara
(74) *Attorney, Agent, or Firm*—Swabey Ogilvy Renault; Christian Cawthorn

(57) ABSTRACT

The present invention relates to antisense oligonucleotides directed to the human cyclin E gene for inhibiting its expression, and to a method for inhibiting cellular proliferation. The antisense oligonucleotides of the present invention have been designed from the 5' and 3'-untranslated region of the cyclin E gene for inhibiting the expression of the cyclin E gene. These antisense oligonucleotides can be used for research purposes, diagnostics and treatment of disease. Methods for specifically modulating cyclin E expression in cells and tissues using the antisense oligonucleotides are disclosed. Methods for diagnosis, detection and treatment of pathologies involving cyclin E gene are disclosed.

38 Claims, 10 Drawing Sheets

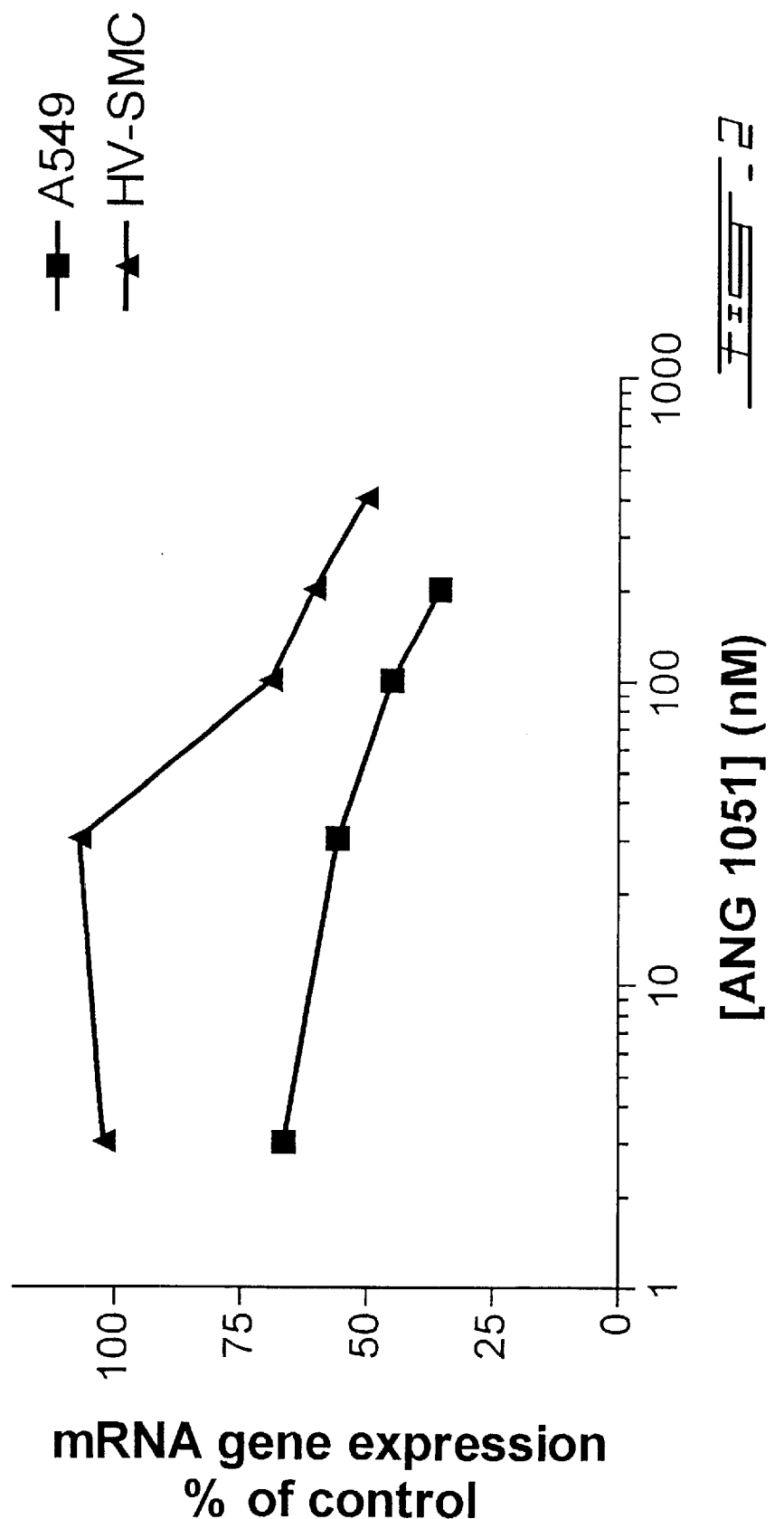

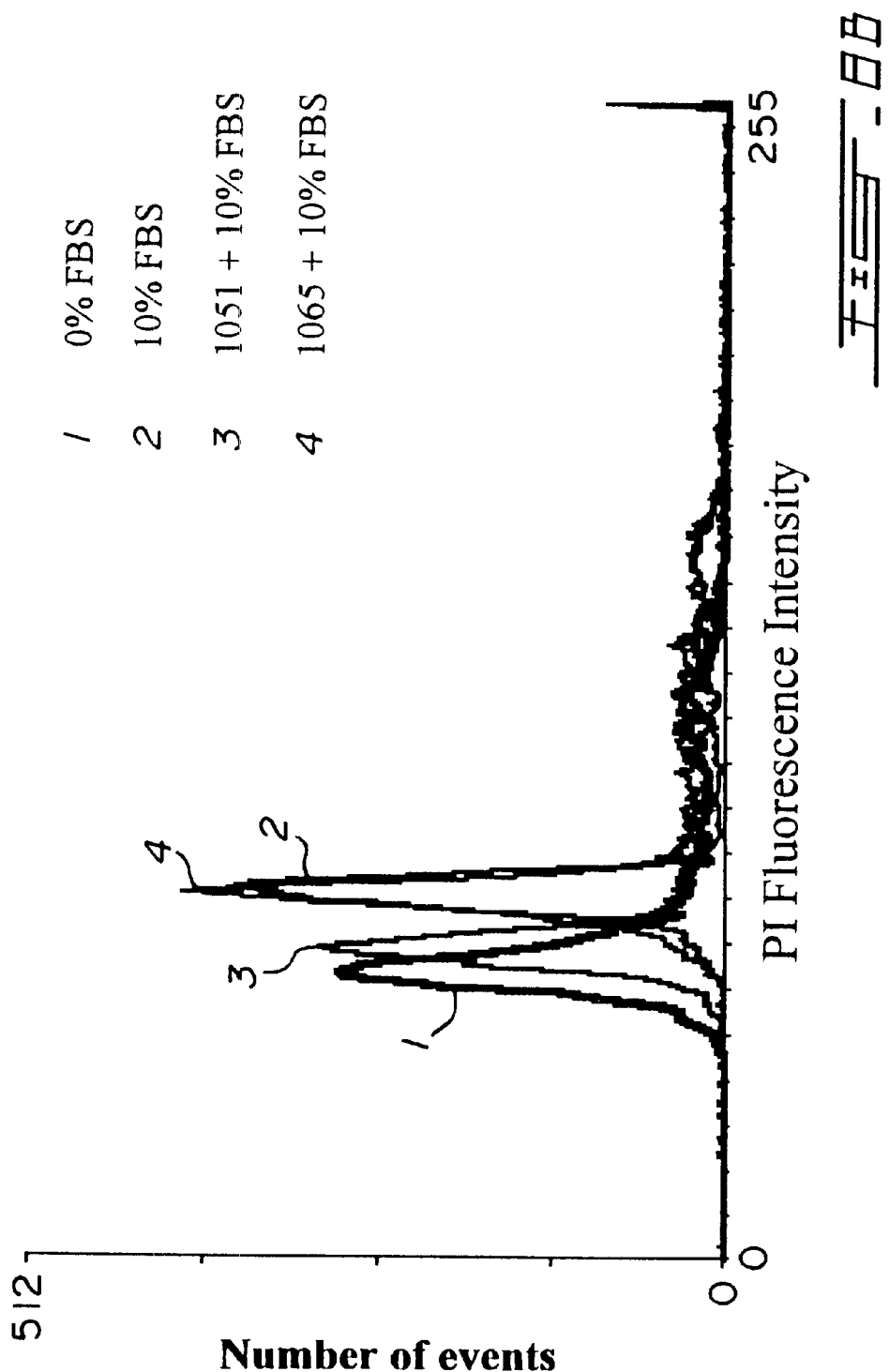

SEQUENCE LISTING

```
<160> NUMBER OF SEQ ID NOS: 14

<210> SEQ ID NO 1
<211> LENGTH: 57
<212> TYPE: DNA
<213> ORGANISM: 5'-UTR Cyclin E gene
<220> FEATURE:
<223> OTHER INFORMATION: Antisense oligonucleotide

<400> SEQUENCE: 1
gtgctcaccc ggcccggtgc cacccgggtc cacagggatg cgaaggagcg ggacacc        57

<210> SEQ ID NO 2
<211> LENGTH: 435
<212> TYPE: DNA
<213> ORGANISM: 3'-UTR Cyclin E gene

<400> SEQUENCE: 2
ccaccccatc cttctccacc aaagacagtt gcgcgcctgc tccacgttct cttctgtctg    60
ttgcagcgga ggcgtgcgtt tgcttttaca gatatctgaa tggaagagtg tttcttccac   120
aacagaagta tttctgtgga tggcatcaaa cagggcaaag tgtttttat tgaatgctta    180 taggtttttt ttaaataagt gggtcaagta caccagccac ctccagacac cagtgcgtgc   240
tcccgatgct gctatggaag gtgctacttg acctaaagga ctcccacaac aacaaaagct   300
tgaagctgtg gagggccacg gtggcgtggc tctcctcgca ggtgttctgg gctccgttgt   360
accaagtgga gcaggtggtt gcgggcaagc gttgtgcaga gcccatagcc agctgggcag   420
ggggctgccc tctcc                                                    435

<210> SEQ ID NO 3
<211> LENGTH: 20
<212> TYPE: DNA
```

```
<213> ORGANISM: Artificial Sequence
<220> FEATURE:
<223> OTHER INFORMATION: Antisense oligonucleotide

<400> SEQUENCE: 3
cctgtggacc cgggtggcac                                               20

<210> SEQ ID NO 4
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 4
ccgctccttc gcatccctgt                                               20

<210> SEQ ID NO 5
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 5
ggtggagaag gatgggtgg                                                20

<210> SEQ ID NO 6
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 6
cgtggagcag gcgcgcaact                                               20

<210> SEQ ID NO 7
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 7
aagcaaacgc acgcctccgc                                               20

<210> SEQ ID NO 8
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 8
tttgccctgt ttgatgccat                                               20

<210> SEQ ID NO 9
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 9
acgcactggt gtctggaggt                                               20
```

```
<210> SEQ ID NO 10
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 10
agcagcatcg ggagcacgca                                                    20

<210> SEQ ID NO 11
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 11
tggccctcca cagcttcaag                                                    20

<210> SEQ ID NO 12
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 12
caacggagcc cagaacacct                                                    20

<210> SEQ ID NO 13
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 13
atgggctctg cacaacgctt                                                    20

<210> SEQ ID NO 14
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 14
gctggctatg ggctctgcac                                                    20
```

ANTISENSE OLIGONUCLEOTIDE MODULATING CYCLIN E GENE EXPRESSION AND THERAPEUTIC USES THEREOF

RELATED APPLICATION

The present application claims priority under 35 U.S.C. §119(e) of previously filed application Ser. No. 60/140,446, filed Jun. 23, 1999, which is now abandoned.

BACKGROUND OF THE INVENTION (a) Field of the Invention

The present invention relates to therapies, diagnostics and research reagents for disease states, which respond to the alteration of cyclin E gene expression, a gene involved in the cell cycle. More particularly, the invention relates to the use of antisense oligonucleotides, which hybridizes to a nucleic acid sequence coding for the cyclin E gene. The invention also relates to a method for preventing restenosis or for treating pathologies, which involves cyclin E gene, such as vascular proliferative diseases or other proliferative disorders such as psoriasis, cancer and related metastasis.

(b) Description of Prior Art

Cell duplication of mammalian cells is regulated by a large number of genes by which their expression of functions responds to mitogenic stimuli (Lanahan A. et al., *Mol. Cell. Biol.*, 12:3919–3929, 1992). Cyclins are prime regulators of cell proliferation, which control the progression of cells through the cell cycle. They function by forming a complex with a class of protein kinases, i.e. cyclin-dependent kinases that are essential for cell cycle transitions (Nigg E A., *Bioessays*, 17(6):471–80, 1995). Normal quiescent cells are in the initial $G_0$ phase. Cells enter the cell cycle under mitogenic stimulation via the G1 phase whereas cyclin D plays a regulatory role to ensure progression through the phase. Cyclin E regulates the entry of cells into the S phase and cyclin A ensures the progression through the S phase. Cyclins A and B ensure the progression through the G2 and M phases of the cell cycle, respectively.

Dysregulation of the G1 phase cyclins, more specifically cyclin E, has been implicated in abnormal cell proliferation. For example, cyclin E overexpression has been reported in rat esophageal tumorigenesis (Wang Q-S et al., *Carcinogenesis*, 17(8): 1583–1588, 1996), in the formation of human hepatic tumors (Tsuji T. et al. *Biophys. Res. Comm.*, 242: 317–321, 1998), in ovarian cancer (Marone M. et al., *Int. J. Cancer*, 75:34–39), in breast cancer (Keyomarsi K et al., *Oncogene*, 11:941–950, 1995), colorectal carcinoma (Leach F. S. et al., *Cancer Res.*, 53:1986–1989, 1993), gastric carcinoma (Akama Y. et al., *Jpn. J. Cancer Res.*, 86:617–621, 1995) and acute lymphoblastic leukemia (Scuderi R. et al., *Blood*, 87:3360–3367, 1996).

Cyclin E is also implicated in abnormal cell proliferation following percutaneous transluminal angioplasty (PCTA) (Wei G L. et al., *Circ. Res.*, 80:418–426, 1997). PCTA is an accepted form of treatment of coronary and peripheral vascular disease. Since its introduction in 1977 for the treatment for coronary disease, primary success rates have reached very high levels (90% to 95%) and complication rates of 1% to 5% are now the standards. However, it was observed that narrowing of the dilated vessel would reoccur at the same site within three to six months following the procedure. The incidence of restenosis following balloon angioplasty may be as high as 55% and 65% in the coronary and peripheral arteries, respectively. All pharmacological approaches to prevent the occurrence of restenosis have failed.

A number of mechanical alternatives to balloon angioplasty have been developed and investigated. However, none of these alternatives have yet shown to diminish conclusively the incidence of restenosis following percutaneous revascularization, except for a modest reduction obtained with the Palmaz-Schatz stent in selected patients. This effect is explained by the propensity of the stent to achieve a consistently greater increase in lumen diameter immediately after the procedure by limiting the phenomenon of elastic recoil. Although many of the risk factors for restenosis have been identified, most of them are difficult to influence.

PCTA results in unavoidable vessel wall injury. Disruption of endothelial and vessel wall structure triggers molecular and cellular events, which leads in some patients to restenosis. Several growth factors, cytokines and cell-surface receptors have been implicated in the proliferation process. In animal models of vascular injury, following the immediate loss of lumen diameter accounted by elastic recoil, an important cascade of events leads to smooth muscle cell (SMC) proliferation that begins 24 hours post-angioplasty. SMC proliferation appears to be a consistent response to balloon dilatation and/or denudation of the artery. Cell replication has been reported to peak within seven days after the angioplasty. Twenty-eight days after the angioplasty, SMC proliferation in the media as well as in the intima appears normalized. This process is then followed by matrix deposition over the next several weeks.

A line of therapy of treatment of uncontrolled cellular proliferation involves radiotherapy. For example, cancerous tumors are treated with radiation therapy, either by external radiation or by applying the radioactive source internally. Another example is the use of a radioactive wire, catheter, stent or balloon that may be applied to an artery undergoing a PCTA procedure. Recently, a procedure involving the infiltration of a radiolabeled oligonucleotide into the vessel wall has been proposed (U.S. Pat. No. 5,821,354).

Pharmacological compounds have been extensively used for cancer therapy with success in a wide array of cancer subtypes. However, these compounds have not proven to succeed in reducing restenosis.

A new avenue of treatment of arteries undergoing PCTA is to locally deliver drugs. In a rat model, antisense oligonucleotides directed against proliferating-cell nuclear antigen (PCNA) (Simons M. et al., *J. Clin. Invest.*, 93(6):2351–2356, 1994) inhibits the SMC proliferation into the intima. The oligonucleotide was mixed in a Pluronic gel that was applied to the artery following the PCTA procedure. Other studies involved the use of antisense c-myb, c-myc and CDK2 kinase oligonucleotides.

Villa and colleagues (Villa A E et al., *Circ. Res.*, 76(4): 505–513, 1995) have unsuccessfully tried to use antisense c-myb oligonucleotides to inhibit restenosis following PCTA in the rat model. They reported that the presence of four contiguous guanine residues might be associated with an aptamer effect, which can be differentiated from a hybridization-dependent antisense mechanism.

Studies have also investigated c-myc antisense oligonucleotides in the prevention of restenosis. Shi and colleagues (Shi Y. et al., *Circulation*, 90 (2): 944–951, 1994) reported that they have successfully reduced smooth muscle proliferation and extracellular matrix accumulation in the lumen of the porcine coronary artery. However, clinical trials using this therapy was deemed unsuccessful (Holt C. M., Antisense Oligonucleotides for the treatment of coronary restenosis. Antisense 98, London. Oct. 8–9, 1998).

Whether the oligonucleotide or the transport delivery device was in fault was not determined.

Other studies have examined the effects of antisense CDK2 oligonucleotides in the prevention of neointimal formation in murine coronary allografts (Suzuki J.-I. et al., *Nat. Med.,* 3(8):900–903, 1997). They reported that intraluminal administration of antisense CDK2 kinase oligonucleotides, a cell cycle regulatory gene, could inhibit neointimal formation after cardiac transplantation.

However, there are no studies up to date that have evaluated the use of antisense oligonucleotides targeting a cell cycle in the reduction of neointimal proliferation. A previous study has shown that certain genes implicated in the cell cycle progression were induced following a PCTA (Wei G L. et al., *Circ. Res.,* 80:418–426, 1997). Indeed, rat arteries subjected to PCTA do express in the following days CDK2, PCNA and cyclin E and A gene products.

The role of cyclin E is to push the cells from the G1 phase of the cell cycle to the S phase, where cells are committed to divide. To date, there is no studies involving antisense constructs nor oligonucleotides that have been reported to inhibit the cyclin E gene product.

It would be highly desirable to be provided with a more effective method and a pharmaceutical composition for preventing uncontrolled cell proliferation, such as restenosis, cancer and psoriasis.

SUMMARY OF THE INVENTION

One aim of the present invention is to provide a more effective method for preventing uncontrolled cell proliferation, such as restenosis.

Another aim of the present invention is to provide a pharmaceutical composition for preventing uncontrolled cell proliferation.

In accordance with the present invention there is provided an antisense oligonucleotide for inhibiting cellular proliferation, said oligonucleotide being complementary to a 5' untranslated region (5'-UTR) or to a 3' untranslated region (3'-UTR) of cyclin E gene for inhibiting the expression of said cyclin E gene, thus inhibiting cellular proliferation.

Preferably, the antisense oligonucleotide has a nucleic acid sequence derived from SEQ ID NO:1 or SEQ ID NO:2.

The cellular proliferation may either be restenosis, or may be caused by a cancer or by psoriasis.

Also in accordance with the present invention there is provided a pharmaceutical composition comprising an antisense oligonucleotide as defined above, in combination with a pharmaceutically acceptable carrier.

Further in accordance with the present invention, there is provided a method for preventing cellular proliferation comprising the step of administering to a patient an antisense oligonucleotide complementary to a 5' untranslated region (5'-UTR) or to a 3' untranslated region (3'-UTR) of cyclin E gene for inhibiting the expression of said cyclin E gene, thus inhibiting cellular proliferation. The antisense oligonucleotide, as described above, may have a nucleic acid sequence derived from SEQ ID NO:1 or SEQ ID NO:2.

The antisense oligonucleotide is preferably delivered at a site of dilatation of an artery, in case of restenosis.

Also in accordance with the present invention, there is provided an antisense oligonucleotide for inhibiting cellular proliferation. The antisense oligonucleotide, as described above, is complementary to a 5' untranslated region (5'-UTR) or to a 3' untranslated region (3'-UTR) of cyclin E gene for inhibiting the expression of said cyclin E gene, thus inhibiting cellular proliferation.

BRIEF DESCRIPTION OF THE DRAWINGS

FIG. 1 illustrates a bar graph of cyclin E mRNA expression in A549 cells following treatment with antisense oligonucleotides hybridizable with the cyclin E gene (ANG 1045, 1048, 1049, 1050, 1051, 1052, 1053, 1054, 1056 and 1057 represent SEQ ID NOS: 3, 5, 6, 7, 8, 9, 10, 11, 12 and 13 respectively.);

FIG. 2 illustrates a line graph of the effects of various concentrations of ANG 1051 (SEQ ID NO:8) on the reduction of cyclin E mRNA expression of the cyclin E gene in two human cell types, A549 cells and saphenous vein smooth muscle cells;

FIGS. 8A and 8B illustrate the effects of ANG 1051 SEQ ID NO:8 and it's 12 base mismatch control ANG 1065 on the cell cycle of saphenous vein smooth muscle cells (FIG. 8A) and A549 cells (FIG. 8B)

DETAILED DESCRIPTION OF THE INVENTION

Figure 3A:
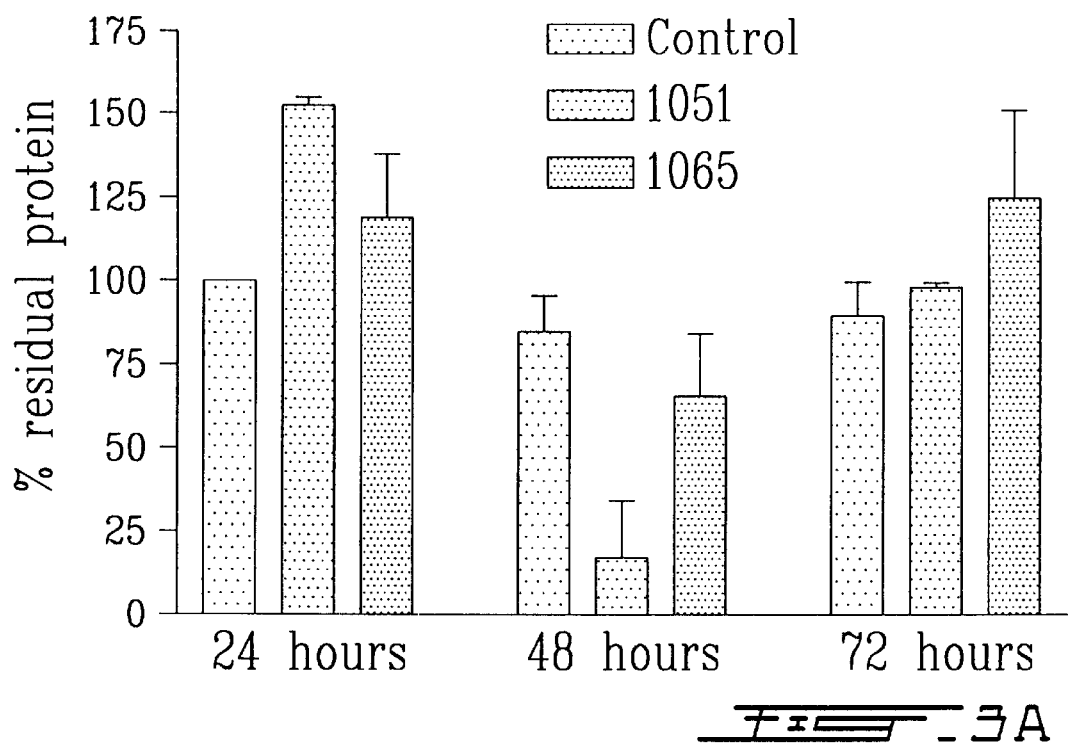
FIGS. 3A and 3B illustrate bar graphs of the effects of 400 nM of ANG 1051 SEQ ID NO:8 and its 12 base mismatch control ANG 1065 on the reduction of cyclin E protein expression of the cyclin E gene in two human cell types, saphenous vein smooth muscle cells (FIG. 3A) and A549 cells (FIG. 3B) as a function of time.

In accordance with the present invention, there is provided a method for preventing proliferative diseases such as restenosis by delivering an antisense oligonucleotide specific for inhibiting the expression of cyclin E gene. The method of the present invention is now feasible with the recent development of site-specific drug delivery for vascular Teiger E et al., *J. Cardiovasc. Pharmacol.,* 33(5):726–732, 1999). Moreover, a systemic delivery of this compound is proven to be effective in preventing this pathology.

The antisense oligonucleotides of the present invention are complementary to nucleic acid sequences such as DNA or RNA derived from human cyclin E gene. The oligonucleotides are comprised of nucleotide units sufficient in identity and number to hybridize specifically to the complementary sequence. This relationship is commonly denominated as "antisense".

In a preferred embodiment, the oligonucleotides are specifically complementary or hybridizable with the 5'-untranslated (5'-UTR) or 3'-untranslated (3'-UTR) regions of the gene.

In another embodiment, the oligonucleotides are specifically hybridizable with DNA or mRNA encoding a particular cyclin isozyme, or a particular set of cyclin isozymes. Such oligonucleotides may be conveniently and desirably presented in a composition comprising a pharmaceutically acceptable carrier.

It is preferred that the oligonucleotides are modified to increase their resistance to metabolic degradation. It is also preferred that increased resistance to nucleases is conveyed by at least one sulfur-containing nucleotide, most preferably a phosphorothioate or phosphorodithioate.

In accordance with other preferred embodiments, the oligonucleotides comprise one or more chemical modifications which convey some desired characteristic such as improved target affinity, cellular uptake, tissue uptake or stability in the presence of cellular nucleases.

Examples of some preferred oligonucleotides are those, which contain modified intersugar linkages. Most preferred are those with $CH_2$—NH—O—$CH_2$, $CH_2$—N($CH_3$)—O—$CH_2$, $CH_2$—O—N($CH_3$)—$CH_2$, $CH_2$—N($CH_3$)—N($CH_3$)—$CH_2$ AND O—N($CH_3$)—$CH_2$—$CH_2$ backbones (where phosphodiester is O—P—O—$CH_2$). Phosphorothioates are also most preferred. Oligonucleotides having a morpholino backbone structure (Summerton, J. E. and Weller D. D., U.S. Pat. No. 5,034,506) or a peptide nucleic acid (PNA) backbone (P. E. Nielson, M. Egholm, R. H. Berg, O. Buchardt, *Science* 1991, 254: 1497) are also preferred. In accordance with other preferred embodiments, the phosphodiester bonds are substituted with structures that are chiral and enantiomerically specific.

Other examples of modified oligonucleotides include species that include at least one modified nucleobase. Thus, purines and pyrimidines other than those normally found in nature may also be employed. The pentofuranosyl portion of the nucleotide subunit may also be modified. Examples of such modifications at the 2' position of sugar moieties which are useful in the present invention but not restricted to are F, Cl, Br, CN, $CF_3$, $SOCH_3$, $N_3$, $NO_2$, $NH_2$, OH, OCN, $OCH_2CH_2OCH_3$, $OCH_3$, $OCH_2CH_3$, $OCH_2OCH_2CH_3$, $O(CH_2)_n NH_2$, where n is from 1 to about 25, SH, $SCH_3$, N-alkyl, $SO_2CH_3$, $ONO_2$, heterocycloalkyl, heterocycloalkaryl, aminoalkylamino, polyalkylamino, substituted silyl, an RNA cleaving group, a reporter group. One or more pentofuranosyl groups may be replaced by another sugar, by a sugar mimic such as cyclobutyl or by another moiety which takes the place of the sugar.

In some preferred embodiments, the oligonucleotides of the invention are chimeric or "gapped" oligonucleotides comprising at least one region which is modified to increase binding affinity for the complementary cyclin E mRNA, and a region which is a substrate region for RNase H cleavage. In one such embodiment a RNAse H substrate region is flanked by two regions having increased cyclin E mRNA binding affinity.

Another preferred embodiment is a three component chimeric antisense oligonucleotide where the 3' terminus is comprised of 2'-modified phosphodiester nucleotides, and 2'-modified P-alkyloxyphosphotriester nucleotides; the 5' terminus is attached to an RNase H-activating region of between three and fifteen contiguous phosphorothioate-linked deoxyribonucleotides; the terminal 3' of the oligonucleotide consists of an inverted deoxyribonucleotide, a contiguous stretch of one to three phosphorothioate 2'-modified ribonucleotides, a biotin group and a P-alkyloxyphosphotriester nucleotide.

The method for the prevention of uncontrolled cell proliferation in human, according to a preferred embodiment of the present invention, comprises delivering a therapeutic substance locally or systemically for the treatment of uncontrolled cell proliferation. For example, when the uncontrolled cell proliferation is a restenosis following angioplasty, therapeutic substance may be delivered by site-specific delivery or systemically. However, when the uncontrolled proliferation is cancer or a malignant tumor, the therapeutic substance can be administered alone or coupled, for example, to an antibody, to cationic lipids or to a peptide moiety. Such peptide moieties include, without limitation, Transforming Growth Factor α (TGFα), TGF β, cytokines, and any other growth factors. The antisense oligonucleotide may be given locally, in a site-specific manner, or systemically.

This therapeutic antisense oligonucleotide according to one embodiment of the present invention may be conjugated to other moieties, such as cholesterol, oleic acid or linoleic acid, to favorably influence its pharmacokinetic properties. It may also be conjugated with an antibody to increase its cell specificity. The antisense oligonucleotide may also be conjugated to a nuclease or other active moieties that may induce cleavage of the target mRNA or DNA strand. The therapeutic properties of the molecule stems from the sequence used to target cyclin E gene products.

To assess the effects of depletion of the cyclin E gene products on cellular processes by oligonucleotide administration, a series of antisense phosphorothioate were designed and synthesized. The most preferred oligonucleotide, ANG 1051, was tested in various assays to assess the biological effects of cyclin E gene product depletion.

In FIG. 1, the oligonucleotides are arranged by cyclin E target regions, in a 5' to 3' direction.

The oligonucleotides of the present invention have been designed to target the 5'- and 3'-UTR to inhibit cyclin E gene expression. Therefore, the oligonucleotides of the present invention may be derived from the 5'-UTR sequence:

gtgctcaccc ggcccggtgc cacccgggtc cacagggatg cgaaggagcg ggacacc (SEQ ID NO:1), or the 3'-UTR sequence:
ccaccccatc cttctccacc aaagacagtt gcgcgcctgc tccacgttct cttctgtctg ttgcagcgga ggcgtgcgtt tgctttaca gatatctgaa tggaagagtg tttcttccac aacagaagta tttctgtgga tggcatcaaa cagggcaaag tgttttttat tgaatgctta taggtttttt ttaaataagt gggtcaagta caccagccac ctccagacac cagtgcgtgc tcccgatgct gctatggaag gtgctacttg acctaaagga ctcccacaac aacaaaagct tgaagctgtg gagggccacg gtggcgtggc tctcctcgca ggtgttctgg gctccgttgt accaagtgga gcaggtggtt gcgggcaagc gttgtgcaga gcccatagcc agctgggcag ggggctgccc tctcc (SEQ ID NO:2)

More preferable, the oligonucleotides have one of the following sequences:

| ANG 1045 | CCTGTGGACC CGGGTGGCAC | (SEQ ID NO:3) |
| ANG 1046 | CCGCTCCTTC GCATCCCTGT | (SEQ ID NO:4) |
| ANG 1048 | GGTGGAGAAG GATGGGGTGG | (SEQ ID NO:5) |
| ANG 1049 | CGTGGAGCAG GCGCGCAACT | (SEQ ID NO:6) |
| ANG 1050 | AAGCAAACGC ACGCCTCCGC | (SEQ ID NO:7) |
| ANG 1051 | TTTGCCCTGT TTGATGCCAT | (SEQ ID NO:8) |
| ANG 1052 | ACGCACTGGT GTCTGGAGGT | (SEQ ID NO:9) |
| ANG 1053 | AGCAGCATCG GGAGCACGCA | (SEQ ID NO:10) |

```
                    -continued
ANG 1054    TGGCCCTCCA CAGCTTCAAG    (SEQ ID NO:11)

ANG 1056    CAACGGAGCC CAGAACACCT    (SEQ ID NO:12)

ANG 1057    ATGGGCTCTG CACAACGCTT    (SEQ ID NO:13)

ANG 1058    GCTGGCTATG GGCTCTGCAC    (SEQ ID NO:14)
```

These oligonucleotides have been found to modulate the expression of cyclin E expression. However, the most preferred antisense phosphorothioate oligonucleotide, ANG 1051, was subjected to further characterization.

FIG. 2 shows a dose-response experiment in which two (2) human cell lines, the human saphenous vein smooth muscle cells (HS-SMC) and the A549 cells were treated for a period of 4 hours with various concentrations of ANG 1051 (SEQ ID NO:8). The results show that ANG 1051 reduced cyclin E mRNA expression with a $IC_{50}$ of approximately 60 nM in the A549 cells and 400 nM in HS-SMC. This discrepancy could be explained by the differences of oligonucleotide uptake in both cell lines.

Figure 3B:
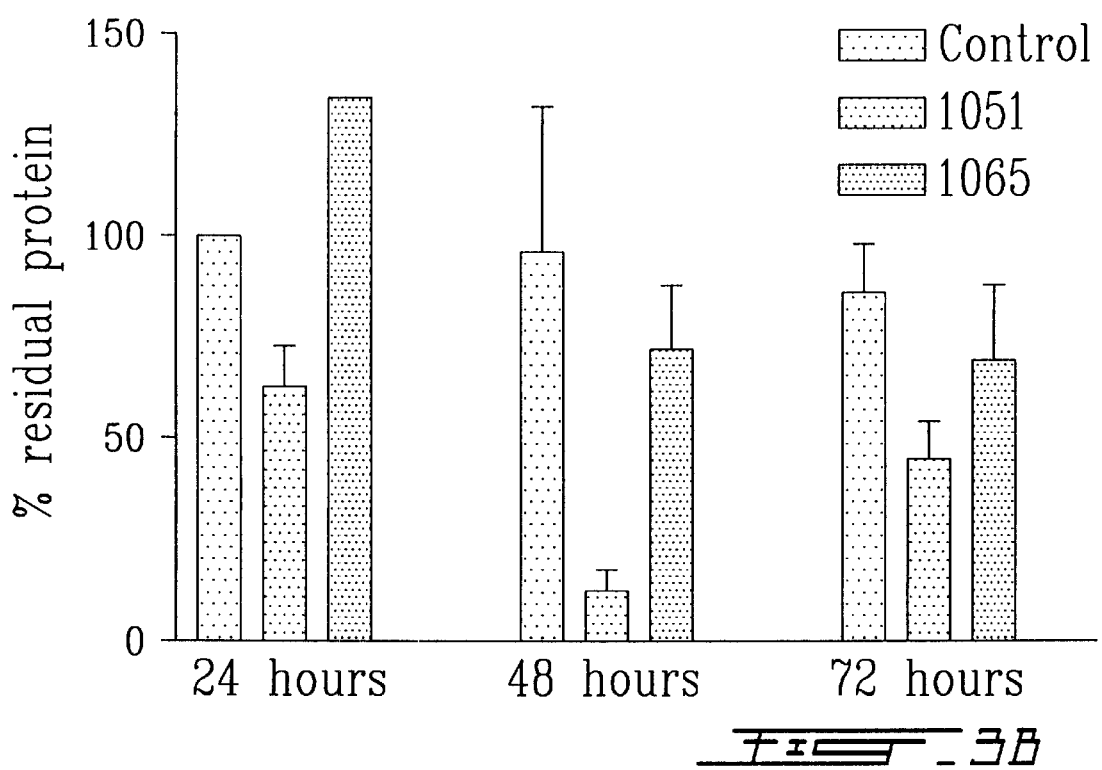

FIGS. 3A and 3B show the cyclin E protein expression in which actively growing HS-SMC (FIG. 3A) or A549 (FIG. 3B) cells are treated with 400 nM of the active oligonucleotide (ANG 1051) (SEQ ID NO 8) and its 12 base mismatch control (ANG 1065) or vehicle. The cells are collected for immunoblotting 24, 48 and 72 hours following the 4-hour treatment of cells with the oligonucleotide. Cyclin E expression is unaffected by treatment of cells with vehicle or ANG 1065. However, cyclin E protein expression is reduced by ANG 1051 hours following treatment. The levels of cyclin E increase after 72 hours.

The lack of effect at 24 hours is due to the presence of constitutive cyclin E protein present at the moment of treatment with the oligonucleotides. The arrest of mRNA translation will be followed by cyclin E protein metabolism. Thus, protein content will decline after 48 hours. However, metabolism of the oligonucleotide will reinitiate translation activities of the cyclin E mRNA yielding to restored levels of cyclin E protein.

Figure 4A:
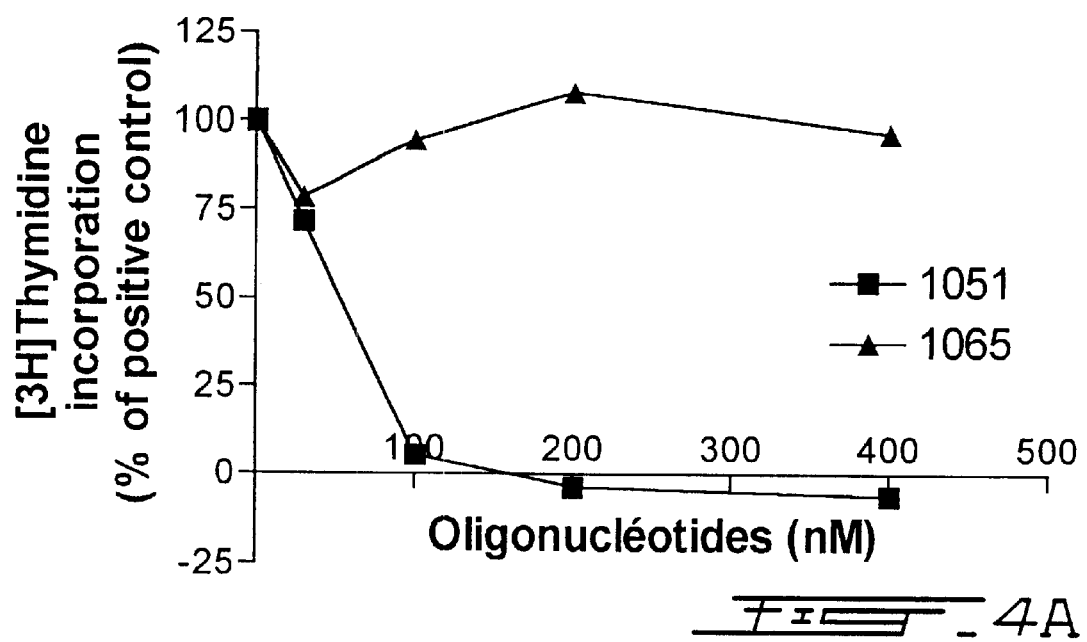
FIGS. 4A and 4B illustrate a line graph of the effects of various concentrations of ANG 1051 SEQ ID NO:8 and its 12 base mismatch control ANG 1065, on tritiated thymidine incorporation of saphenous vein smooth muscle cells (FIG. 4A) and A549 cells (FIG. 4B)
Figure 4B:
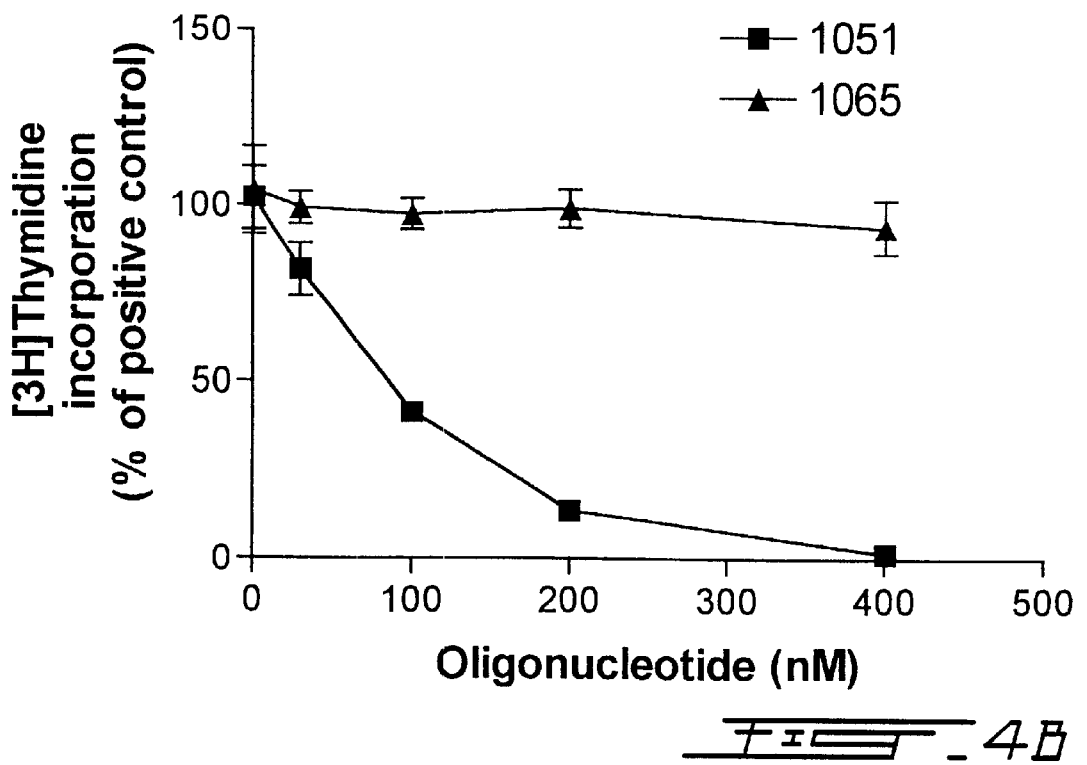

FIGS. 4A and 4B show a dose-response experiment in which HS-SMC (FIG. 4A) and A549 (FIG. 4B) cells were treated with oligonucleotides. Cell proliferation was then measured by tritiated thymidine incorporation.

Cells were rendered quiescent by exposure to low serum media for 24 hours. Various concentrations of oligonucleotides were then applied to cells for 4 hours. Serum levels were then restored to levels that initiates proliferation for 24 hours. Tritiated thymidine was then added to the cells and allowed to incorporate for an additional 24 hours.

Results show that treatment of cells with ANG 1051 for the first 4 hours of the experiment was sufficient to reduce cell proliferation in both cell lines. The control oligonucleotide did not exhibit any effect on cell proliferation, proving that this antisense is sequence specific a phenomenon.

Figure 5:
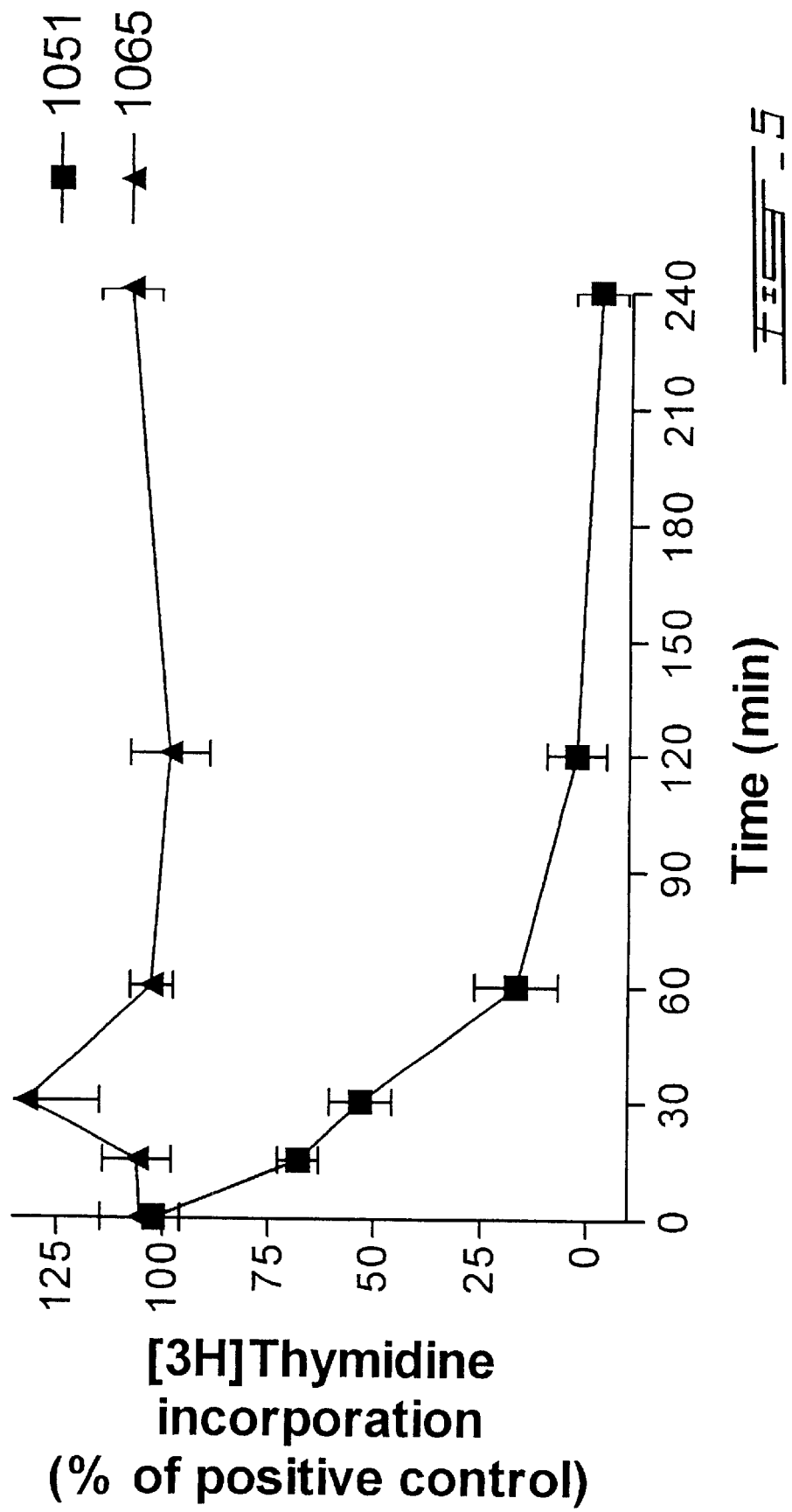
FIG. 5 illustrates a line graph of the effects of 400 nM of ANG 1051 SEQ ID NO:8 and its 12 base mismatch control ANG 1065 on cell number of saphenous vein smooth muscle cells as a function of the exposure time of the oligonucleotides to achieve an anti-proliferative effect.

FIG. 5 shows a time course experiment whereas HS-SMC cells was exposed to oligonucleotides for the times indicated and cell proliferation was then measured by the tritiated thymidine incorporation assay as described for FIGS. 4A and 4B.

Results show that the time of oligonucleotide exposure required to produce the maximal anti-proliferative effect is 120 min. Exposure of cells to oligonucleotides for 60 min produced an 85% reduction while a 30 min exposure time is required to reduce by 50% the anti-proliferative activity of ANG 1051 (SEQ ID NO 8). The mismatch control, its mismatch 12 nucleobase control ANG 1065 has no effect.

Figure 6:
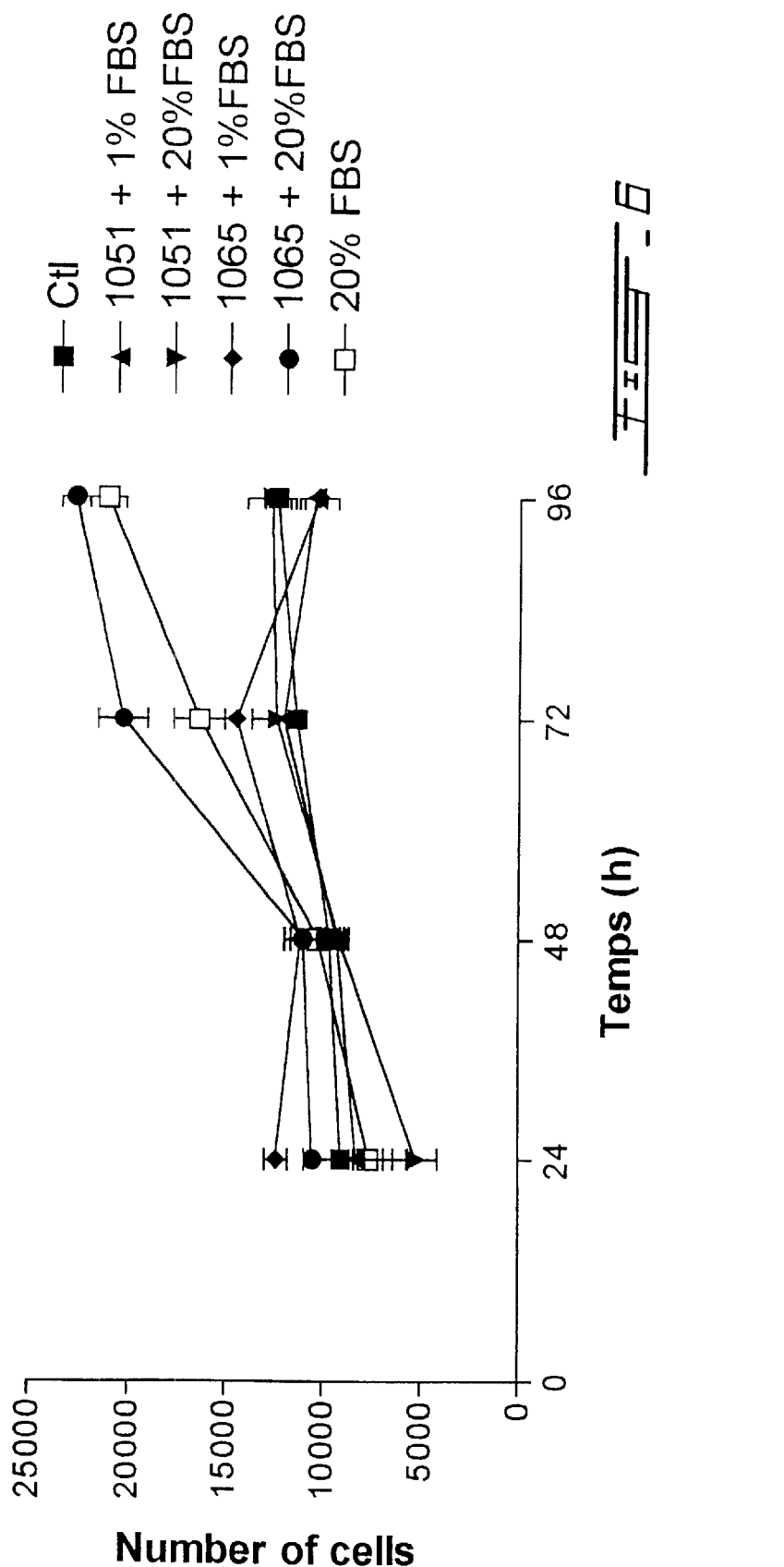
FIG. 6 illustrates a line graph of the effects of 400 nM of ANG 1051 SEQ ID NO:8 and its 12 base mismatch control ANG 1065 on cell proliferation assessed by counting the number of cells using an hemacytometer.

FIG. 6 shows a time course experiment whereas HS-SMC cells were treated with oligonucleotides then cell proliferation was assessed by counting the number of cells using an hemacytometer.

Figure 7:
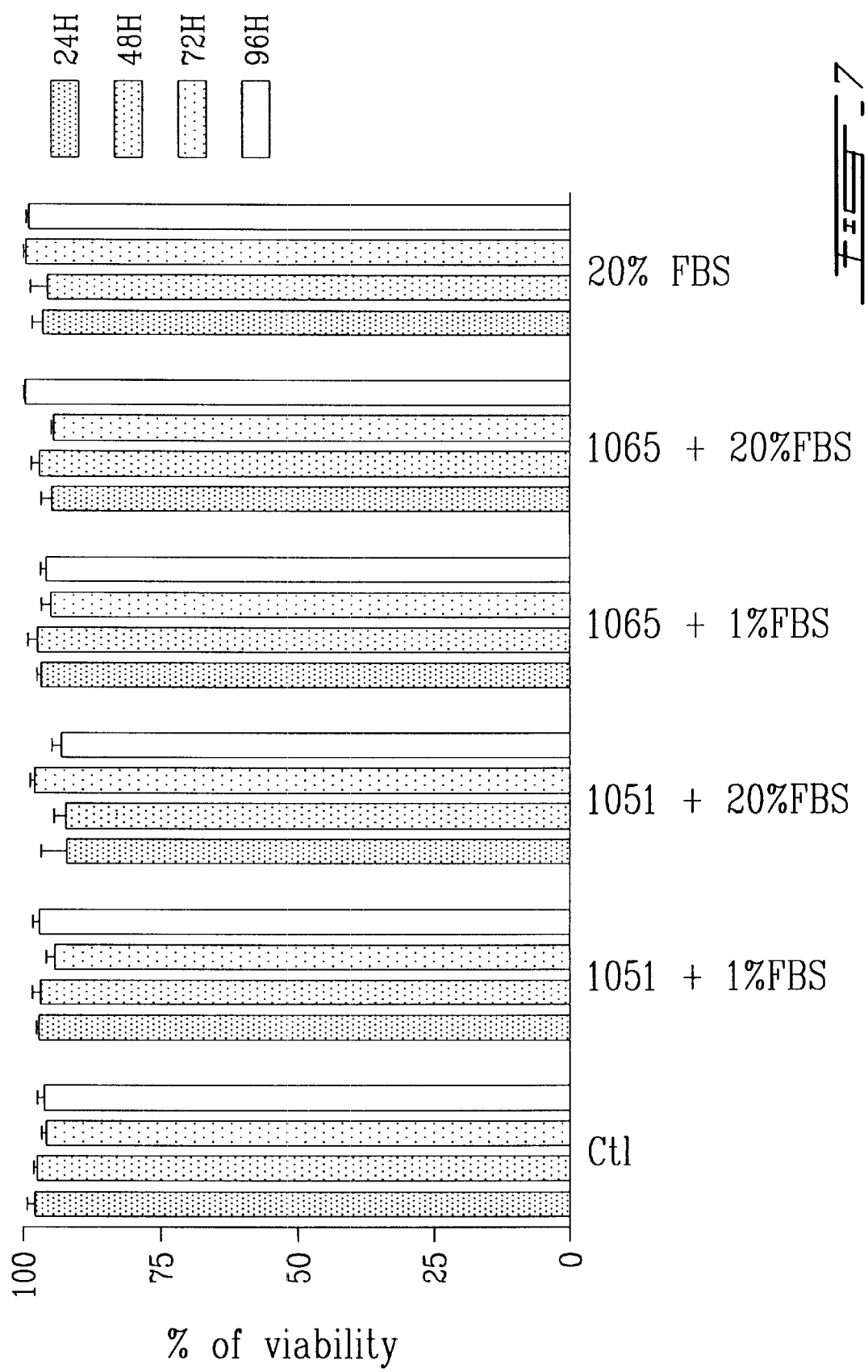
FIG. 7 illustrates a bar graph of the effects of 400 nM of ANG 1051 SEQ ID NO:8 and its 12 base mismatch control ANG 1065 on cell viability of saphenous vein smooth muscle cells as a function of time.

Cells were plated at a density of 15,000 cells/well then were rendered quiescent by exposure to low serum media for 24 hours. Oligonucleotides (400 nM) were applied to cells for 4 hours and then, when indicated, the serum levels were restored to initiate proliferation. Cells were counted in a trypan blue solution at the times indicated. Cell viability data is represented in FIG. 7.

Results for cell proliferation show that cells exposed to low serum media (1% FBS) do not proliferate. Conditions where cells were treated with ANG 1051 SEQ ID NO 8 or mismatch control ANG 1065 and exposed to low serum media did not exhibit toxicity. Cells remained plated into the well and in a quiescent stage.

Cells treated with ANG 1065 and vehicle which were incubated with complete media (20% FBS) proliferated, doubling its population. However, the antisense phosphorothioate ANG 1051 prevented proliferation induced by serum.

These additional results correlate to the prevention of tritiated thymidine incorporation, represented in FIGS. 4A, 4B and 5, demonstrating that oligonucleotide induced depletion of cyclin E gene products exhibits potent antiproliferative properties.

FIG. 7 shows the results of HS-SMC viability in the assay described in FIG. 6. In every condition, oligonucleotides did not induce cell death or toxicity. Cell viability was above 95% in every condition tested at 24, 48, 72 and 96 hours following treatment.

These results indicate that ANG 1051 (SEQ ID NO:8) does not induce HS-SMC kill but induces reproductive cell kill.

Figure 8A:
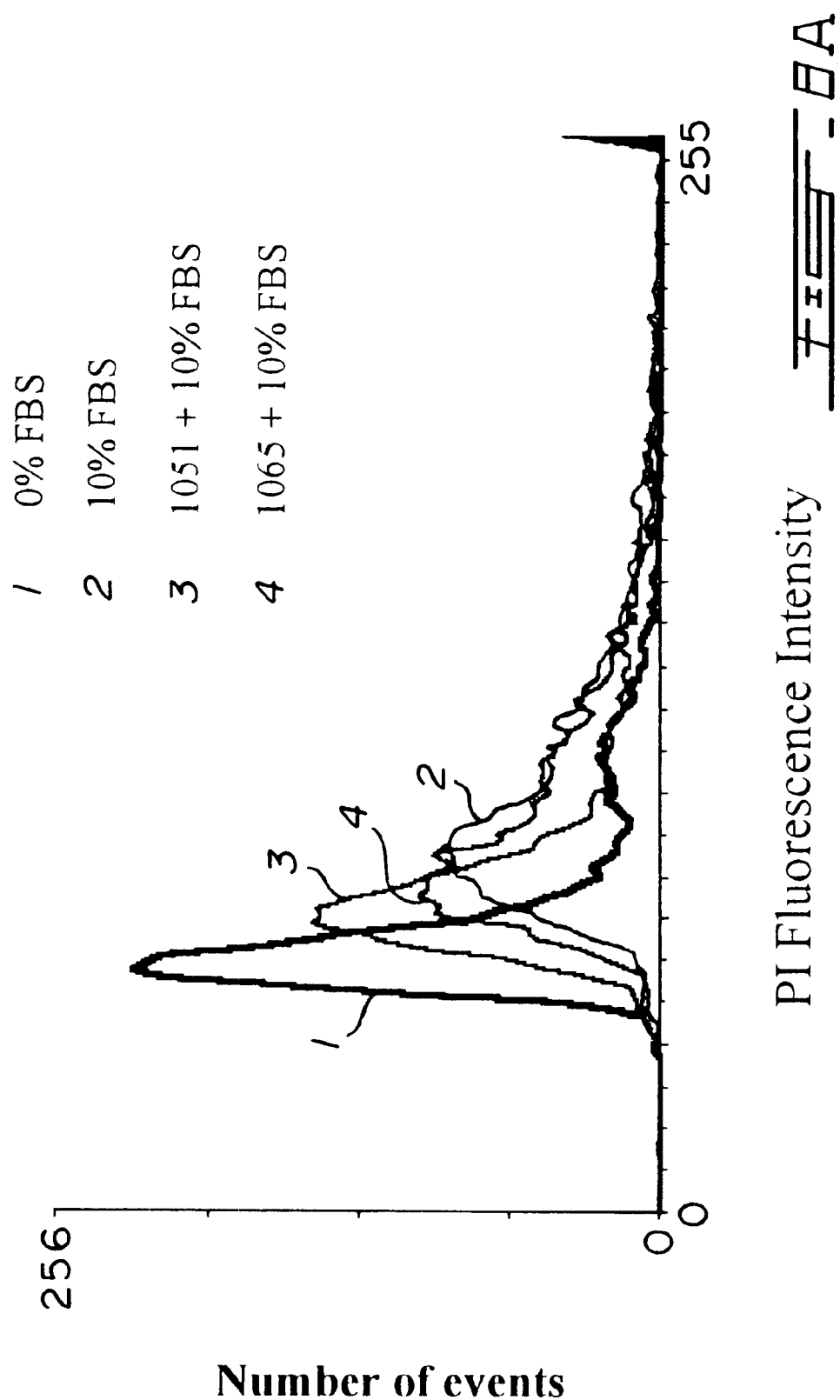

FIGS. 8A and 8B. show the cell cycle progression of HS-SMC (FIG. 8A) and A549 cells (FIG. 8B) following oligonucleotide treatment. Cell cycle progression was measured using propidium iodide staining.

The cells were rendered quiescent by exposure to low serum media for 72 hours. Oligonucleotides (400 nM) were then applied to the cells for 4 hours. The serum levels were then restored to levels that initiate proliferation. Cells were harvested 22 hours after serum stimulation.

The results show that the treatment of cells with ANG 1051 inhibits the entry of cells into the S phase. The control oligonucleotide did not exhibit any effects on the cell cycle, proving that this is an antisense mediated effect since it is sequence specific phenomena.

Figures 9A, 9B:
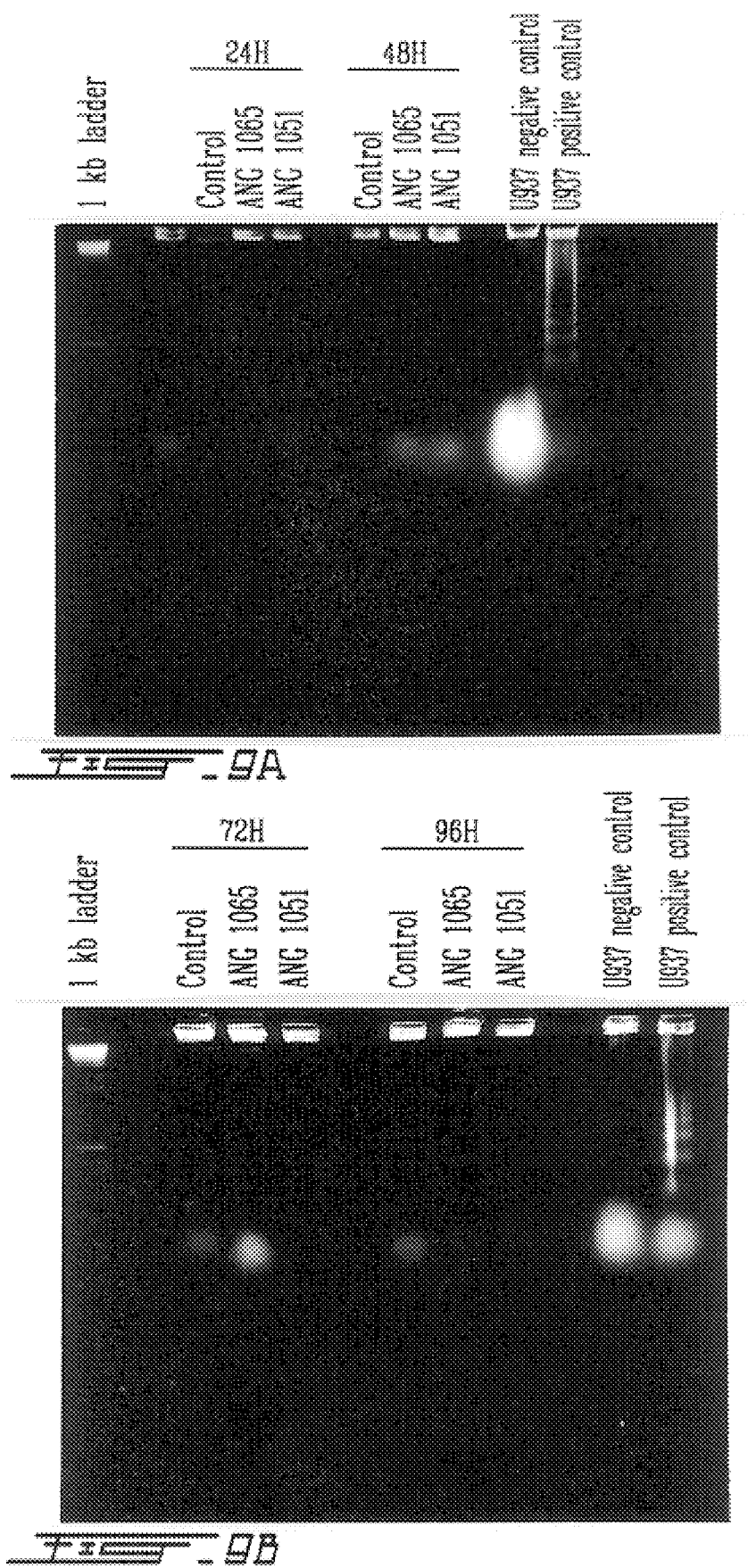
FIGS. 9A and 9B illustrates gels representing DNA fragmentation after 24 and 48 hours (FIG. 9A) and 72 and 96 hours (FIG. 9B) following treatment of cells with 400 nM of oligonucleotides.

FIGS. 9A and 9B show the potential effects of ANG 1051 SEQ ID NO:8 and mismatch control ANG 1065 on apoptosis of HS-SMC. Cells were rendered quiescent by exposure to low serum media for 24 hours. Oligonucleotides (400 nM) were applied to cells for 4 hours then, the serum levels were restored to initiate proliferation. Cells were collected 24 and 48 hours (FIG. 9A) and 72 and 96 hours (FIG. 9B) following treatment to assess DNA fragmentation.

Results indicate that neither ANG 1051 nor ANG 1065 induced apoptosis in HS-SMC cells. This further demonstrates that cyclin E gene products depletion by ANG 1051 does not induce HS-SMC kill but induces reproductive cell kill.

For preventing restenosis, the oligonucleotides of the present invention may be combined with other therapeutic modalities that have been shown efficient in arteries such as coronary stenting. A local drug delivery strategy or a systemic delivery based on the use of the invention presented herein may be applicable to all vascular proliferative disorders. These disorders may be, but not limited to, coronary and peripheral arterial restenosis, arterio venous fistulas, etc. and cancer and metastasis therapy and psoriasis and other pathologies which involves cyclin E gene.

The present invention will be more readily understood by referring to the following examples, which are given to illustrate the invention rather than to limit its scope.

EXAMPLE I

Oligonucleotide Synthesis and Purification

Substituted and unsubstituted deoxyoligonucleotides were synthesized on an automated DNA synthesizer (Perseptive BioSystems model 8909) using fast deprotecting phosphoramidite chemistry and the DMT groupment remaining on the 5' end of the oligonucleotide. For phosphorothioate oligonucleotides, the standard oxidation bottle was replaced by 0.024 M solution of 3-ethoxy-1,2,4-diathiazoline-5-one in acetonitrile for the stepwise thiation of the phophite linkages. After cleavage from the CPG column and deblocking in concentrated ammonium hydroxide at 55° C. for a minimum of 15 min, the dimethoxytrityl (DMT) bearing oligonucleotides were purified on a HPLC system on a Oligo R3™ reverse phase column (Perseptive Biosystems, MA) using the scheme depicted in Table 1 and the following gradient:

| Solution A: | 0.12M Glacial Acetic acid - 0.16M triethylamine; |
|---|---|
| Solution B: | 80% Acetonitrile - 20% water; |
| Solution C: | 3% trifluoroacetic acid (TFA); and |
| Solution D: | bidistillated water. |

TABLE 1

| Step # | Time (min) | Flow | % A | % B | % C | % D | Comments |
|---|---|---|---|---|---|---|---|
| 1 | 0 | 5 | 85 | 15 | 0 | 0 | Elimination of |
| 2 | 3 | 5 | 85 | 15 | 0 | 0 | failure sequences |
| 3 | 4 | 5 | 0 | 0 | 0 | 100 | Buffer Wash |
| 4 | 7.5 | 5 | 0 | 0 | 0 | 100 | Cleavage of |
| 5 | 8.5 | 5 | 0 | 0 | 100 | 0 | DMT |
| 6 | 9 | 5 | 0 | 0 | 0 | 100 | TFA Wash |
| 7 | 15 | 5 | 0 | 0 | 0 | 100 | |
| 8 | 18 | 5 | 0 | 0 | 0 | 100 | Collect Sample |
| 9 | 21 | 5 | 0 | 20 | 0 | 80 | |
| 10 | 22 | 5 | 0 | 20 | 0 | 80 | |
| 11 | 25 | 5 | 0 | 100 | 0 | 0 | Column Wash |
| 12 | 26 | 5 | 0 | 100 | 0 | 0 | |
| 13 | 31 | 5 | 85 | 15 | 0 | 0 | Equilibrate |
| 14 | 31.1 | 0 | 85 | 15 | 0 | 0 | Column |

The oligonucleotide was purified using a multi-solvent step gradient. The first step was to eliminate the failure sequences from the final product. Only the final product bears the DMT (dimethoxytrityl) moiety, which will remain in the reverse phase column. This step will be followed by a washing step to desalt the oligonucleotide. The next step involves elimination of the DMT moiety by briefly exposing the oligonucleotide to trifluoroacetic acid (TFA).

The TFA is washed and a gradient is then applied to elute the purified oligonucleotide at approximately 18 to 19 minutes. Then, the column is washed and equilibrated for the next run.

EXAMPLE II

Melting Curves

Absorbance vs temperature curves were measured at 260 nm using a Gilford 260 spectrophotometer interfaced to an IBM PC computer and a Gilford Response II spectrophotometer. The buffer contained 100 nM Na+, 10 mM phosphate and 0.1 mM EDTA, pH 7. Oligonucleotide concentration was 4 μM each strand determined from the absorbance at 85° C. and extinction coefficients calculated according to Puglisi and Tinocco (Methods in Enzymol. 1989, 180, 304–325). Tm values, free energies of duplex formation and association constants were obtained from fits of data to a two-state model with linear sloping baselines. Reported parameters are averages of at least three experiments.

EXAMPLE III

RNase H Analysis

RNase H assays were performed using a chemically synthesized 2'0-base oligoribonucleotide corresponding to the complementary sequence of the active antisense phosphorothioate oligonucleotide. The 5' end-labeled RNA was used at a concentration of 20 nM and incubated with a 10-fold molar excess of antisense oligonucleotide in a reaction containing 20 mM tris-Cl, pH 7.5, 100 mM KCl, 10 mM $MgCl_2$, 1 mM dithiothreitol, 10 μg tRNA and 4 U RNasin in a final volume of 10 μl. The reaction components were preannealed at 37° C. for 15 minutes then allowed to cool slowly to room temperature. A549 cell nuclear extracts were used as a source of mammalian RNase H. Reactions were initiated by addition of 2 μg of nuclear extract and reactions were allowed to proceed for 10 minutes at 37° C. Reactions were stopped by phenol/chloroform extraction and RNA components were precipitated with ethanol. Equal CPMs were loaded on a 20% polyacrylamide gel containing 7 M urea and RNA cleavage products were resolved and visualized by electrophoresis followed by autoradiography. Quantitation of cleavage products was performed using an Instant Imager (Packard, Downers Grove, Ill.).

EXAMPLE IV

Oligonucleotide Treatment of Cells

HS-SMC or A549 cells were washed with prewarmed non-supplemented DMEM solution at 37° C. The oligonucleotide was then administered in DMEM containing 5 μg/ml N-[1-(2,3-dioleyloxy)propyl]-N,N,N,-trimethylammonium chloride (DOTMA) to each plate (500 μl/well). Each plate is incubated for 4 hours at 37° C. Medium was removed and replaced with complete DMEM media. Cells were then subjected to various biological assays.

EXAMPLE V

Northern Blot Analysis of Cyclin E Expression in vitro

Human lung carcinoma A549 cell line was obtained from the American Type Culture Collection (Rockville, Md.). The human saphenous vein smooth muscle cells (HS-SMC) were prepared from saphenous vein grafts from consenting patients. Cells were grown in DMEM supplemented with 10% or 20% heat inactivated fetal bovine serum for A549 and HS-SMC, respectively and 50 U/ml each of penicillin and streptomycin. Cells were seeded on 100 mM plates. When they reached 70–80% confluency, they were treated with oligonucleotide as described in EXAMPLE IV. Media was then replaced with DMEM and cells were harvested 24 hours after oligonucleotide treatment and total RNA was isolated using Qiagen's RNeasy™ Kit.

Northern Hybridization

Ten (10) µg of RNA for each sample was electrophoresed on a 1.2% agarose/formaldehyde gel and transferred overnight to a nylon membrane using standard methods. RNA was UV-crosslinked to the membrane. Double stranded $^{32}$P-probes were synthesized using the Oligolabelling Kit (Pharmacia Upjohn, Montreal, Canada). The probes used in these studies are cyclin E and G3PDH. Blots were prehybridized for 15 minutes at 68° C. with the QuickHyb™ hybridization solution (Stratagene, La Jolla, Calif.). The heat-denatured radioactive probe was added and the membrane was hybridized for 90 min at 68° C. The blots were washed twice for 15 minutes at room temperature with 2×SSC/0.1% SDS and twice for 15 minutes at 56° C. with 0.1×SSC/0.1% SDS. Blots were autoradiographed and the signal was quantified using an Instant Imager (Packard, Downers Grove, Ill.). Northern blots were first hybridized with the cyclin E probe, then stripped by boiling for 5 min in 0.1×SSC/0.1% SDS and rehybridized with the control G3PDH probe to check for correct sample loading.

EXAMPLE VI

Western Blot Analysis of Cyclin E in vitro

HS-SMC or A549 cells were grown in DMEM supplemented with 10% heat inactivated fetal bovine serum and 50 U/ml each of penicillin and streptomycin. Cells were seeded on 100 mM plates. When they reached 70–80% confluency, they were treated with oligonucleotide as described in EXAMPLE IV. Media was then replaced with DMEM and cells were harvested at either 24, 48 or 72 hours after oligonucleotide treatment and total protein were extracted. Cells were washed once with ice cold PBS and lysed in 250 µl of lysis buffer (20 mM Tris-HCl, pH 7.4; 1% (vol/vol) Triton X-100; 5 mM EGTA; 2 mM EDTA; 2 mM dithiothreitol; 50 mM NaF; 10 mM $Na_2HPO_4$) supplemented with leupeptin (2 µg/ml) and aprotinin (1 µg/ml) at 4° C. Samples were loaded equally on gel, as determined by Bradford protein assay (Bio-Rad, Hercules, Calif.), and electrophoresed through a 12% acrylamide gel and then electroblotted. The levels of cyclin E and G3PDH were simultaneously determined by use of a polyclonal anti-cyclin E (1:2000; Upstate Biotechnology, Lake Placid, N.Y.) and monoclonal anti-G3PDH (1:50000; Advanced ImmunoChemical Inc., Long Beach, Calif.) antibodies. After a minimum of 2 hr incubation with the primary antibody, the membranes were incubated with either horse radish peroxidase (HRP) labeled donkey anti-mouse, or HRP-labeled donkey anti-rabbit antibodies (Amersham Pharmacia Biotech, Buckinghamshire, England) for 1 h. Hybridizing bands were visualized using the ECL™ western blotting detection kit (Amersham Pharmacia Biotech, Buckinghamshire, England) and quantified using an Instant Imager (Packard, Downers Grove, Ill.).

EXAMPLE VII

Cell Proliferation Assay

HS-SMC and A549 cells were synchronized with serum-deprived medium for 24 hours. Cells were treated with oligonucleotides as described in EXAMPLE IV then stimulated with FBS. After 24 hours, cells were exposed to [methyl-$^3$H]-thymidine (6.7 Ci/mmol, NEN Life Science Products) for an additional 24 hours. Cells were then washed once in ice-cold PBS and fixed for 15 minutes at 4° C. with an ethanol/acetic acid solution (3:1). Cells were then washed with water and incubated 15 minutes in 0.5 N perchloric acid. Cells were then washed and incubated 1 hour at 80° C. with a 0.5 N perchloric acid solution. The resulting solution was transferred in a scintillation vial and counted.

EXAMPLE VIII

Cell Cycle Progression

HS-SMCs were synchronized in serum-deprived medium for 24 hours. Cells were treated with oligonucleotides as described in EXAMPLE IV then stimulated with FBS. Cells were then harvested 24 and 48 hours after serum stimulation and fixed in a 70% ethanol and treated with 0.1% sodium citrate, 0.3% NP-40, 0.02 RNAse and 0.05 mg/ml propidium iodide. Stained cells were analyzed by flow cytometry with a GACScan model (Becton Dickinson Immunocytometry Systems).

EXAMPLE IX

Kinase Assay

HS-SMCs were synchronized in serum-deprived medium for 24 hours. Cells were treated with oligonucleotides as described in EXAMPLE IV then stimulated with FBS. Cells were then lysed in 50 mM Tris (pH 7.4), 250 mM NaCl and 0.1% NP-40 and clarified by ultracentrifugation at 100,000×g for 30 minutes. Samples were immunoprecipitated using protein A-Sepharose™ with polyclonal anti-cyclin E antibody (Upstate Biotechnology, Lake Placid, N.Y.). Immunoprecipitates were washed with kinase buffer (50 mM Tris pH 7.4, 10 mM $MgCl_2$, 1 mM DTT) supplemented with 0.1 mg/ml BSA.

For the kinase assay, the beads were resuspended in 50 µl of kinase buffer supplemented with 30 µM ATP, 5 µCi of [gamma-$^{32}$P]ATP and 1 µg histone H1. This suspension was incubated at 37° C. for 30 min. Products were analyzed by using a 12% SDS-PAGE gel followed by autoradiography.

EXAMPLE X

Oligonucleotides in Preventing Restenosis
Angiography Procedure

Domestic pigs were sedated with intramuscular injection of ketamin, azaperon and atropine to undergo anesthesia with thiopental sodium (iv). The pigs were intubated and ventilated with a mix of isoflurane 2% and oxygen during the procedure. An 8 Fr. guiding catheter was advanced through a femoral sheath with a 0.035 J guide-wire, under fluoroscopic monitoring in the ascending aorta. The guide wire was then removed, allowing the guiding catheter to be positioned in the ostium of the target vessel. Prior to performing the angiography, a bolus of 1 mL of nitroglycerin solution with a concentration of 0.3 mg/mL is injected intra-coronary. The angiography was then performed in at least two near orthogonal views that visualize the target site of right coronary artery (RCA) or left circumflex artery (LCX) of the pig. A quantitative coronary angiography (QCA) measure was done to assess the vessel size.

Local Drug Delivery Device

A drug delivery device, Infiltrator® catheter (InterVentional Technologies, San Diego, Calif.), was used for intra-mural administration of oligonucleotides. An Infiltrator® catheter was prepared with three-way stopcock on both ports. Air was flushed in the injection port with a 20 cc syringe. Vacuum was done in the balloon port using a 20 cc syringe and maintained with a 10 cc syringe in the usual fashion. An Indeflator® pump was prepared with 50:50 contrast media/sterile water and was attached to the balloon port. The central lumen was flushed with heparinized saline and a 0.014 wire inserted in the lumen of the catheter. The drug was then carefully charged into the injection port (green). The dead volume was filled with the drug solution (0.6 ml). With the guiding catheter in place, the Infiltrator® catheter was advanced over the dilatation wire through the "Y" hub to the coronary ostium. The location of drug delivery device was verified and recorded with an injection of contrast media. After proper positioning of the drug delivery device at the selected site, the balloon was inflated to 2–4 atmospheres. The apposition of the balloon to the vessel wall was verified with contrast media. A total bolus of 0.6 ml of drug was then slowly infused over 60–90 seconds. During the transfection, the ECG was monitored to assess any sign of ischemia. Following drug infusion, the balloon was deflated and the catheter withdrawn. Control angiography was then performed to document any residual luminal stenosis or vessel wall dissection. If spasm was documented, 1 ml of nitroglycerin solution at a concentration of 0.3 mg/ml was injected intra-coronary.

EXAMPLE XI

Oligonucleotide Effects on the Growth of Tumor Cell Lines

Female immunodeficient CD1 mice were obtained from Charles River (St-Laurent, Canada) and used when 6–8 weeks old at onset of treatment. Each mouse was inoculated subcutaneously in the flank with $5 \times 10^6$ tumor cells (A549, MCF-7 and OVCAR 3) in 0.1 ml. Twelve mice per group were be inoculated with the cell lines. Tumor size were be measured twice weekly in two dimensions using a caliper, and the volume expressed in mm3 using the formula: $V=1/2a \times b^2$, where a and b are the long and short diameters of the tumor. Each group contained 6–8 tumor-bearing mice. The rest of the animals were euthanized using $CO_2$ inhalation. Treatment was then initiated when the tumor sizes reaches 70–100 mm$^3$.

Oligonucleotides (formulated in saline) were administered i.v. daily into the tail vein while control animals received saline. Tumor volume was monitored twice or three times weekly and 24 h after the last treatment. Mice were then sacrificed and tumor fragments are stored on dry ice for subsequent northern analysis.

While the invention has been described in connection with specific embodiments thereof, it will be understood that it is capable of further modifications and this application is intended to cover any variations, uses, or adaptations of the. invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. An antisense oligonucleotide for inhibiting cellular proliferation, said antisense oligonucleotide being complementary to a 5' untranslated region (5'-UTR) cyclin E transcript for inhibiting the expression of cyclin E, thus inhibiting cellular proliferation, said antisense oligonucleotide having SEQ ID NO: 3, wherein cellular proliferation is tumor cell proliferation.

2. An antisense oligonucleotide for inhibiting cellular proliferation, said antisense oligonucleotide being complementary to a 3' untranslated region (3'-UTR) of cyclin E transcript for inhibiting the expression of cyclin E, thus inhibiting the cellular proliferation, said antisense oligonucleotide having SEQ. ID NO: 5, wherein cellular proliferation is tumor cell proliferation.

3. An antisense oligonucleotide for inhibiting cellular proliferation, said antisense oligonucleotide being complementary to a 3' untranslated region (3'-UTR) of cyclin E transcript for inhibiting the expression of cyclin E, thus inhibiting the cellular proliferation, said antisense oligonucleotide having SEQ. ID NO: 6, wherein cellular proliferation is tumor cell proliferation.

4. An antisense oligonucleotide for inhibiting cellular proliferation, said antisense oligonucleotide being complementary to a 3' untranslated region (3'-UTR) of cyclin E transcript for inhibiting the expression of cyclin E, thus inhibiting the cellular proliferation, said antisense oligonucleotide having SEQ. ID NO: 7, wherein cellular proliferation is tumor cell proliferation.

5. An antisense oligonucleotide for inhibiting cellular proliferation, said antisense oligonucleotide being complementary to a 3' untranslated region (3'-UTR) of cyclin E transcript for inhibiting the expression of cyclin E, thus inhibiting the cellular proliferation, said antisense oligonucleotide having SEQ. ID NO: 8, wherein cellular proliferation is tumor cell proliferation.

6. An antisense oligonucleotide for inhibiting cellular proliferation, said antisense oligonucleotide being complementary to a 3' untranslated region (3'-UTR) of cyclin E transcript for inhibiting the expression of cyclin E, thus inhibiting the cellular proliferation, said antisense oligonucleotide having SEQ. ID NO: 9, wherein cellular proliferation is tumor cell proliferation.

7. An antisense oligonucleotide for inhibiting cellular proliferation, said antisense oligonucleotide being complementary to a 3' untranslated region (3'-UTR) of cyclin E transcript for inhibiting the expression of cyclin E, thus inhibiting the cellular proliferation, said antisense oligonucleotide having SEQ. ID NO: 10, wherein cellular proliferation is tumor cell proliferation.

8. An antisense oligonucleotide for inhibiting cellular proliferation, said antisense oligonucleotide being complementary to a 3' untranslated region (3'-UTR) of cyclin E transcript for inhibiting the expression of cyclin E, thus inhibiting the cellular proliferation, said antisense oligonucleotide having SEQ. ID NO: 12, wherein cellular proliferation is tumor cell proliferation.

9. An antisense oligonucleotide for inhibiting cellular proliferation, said antisense oligonucleotide being complementary to a 3' untranslated region (3'-UTR) of cyclin E transcript for inhibiting the expression of cyclin E, thus inhibiting the cellular proliferation, said antisense oligonucleotide having SEQ. ID NO: 13, wherein cellular proliferation is tumor cell proliferation.

10. A pharmaceutical composition comprising an antisense oligonucleotide as defined in claims 1 and 2, in combination with a pharmaceutically acceptable carrier.

11. An antisense oligonucleotide for inhibiting cellular proliferation, said antisense oligonucleotide being complementary to a 5' untranslated region (5'-UTR) of cyclin E transcript for inhibiting the expression of cyclin E, thus inhibiting cellular proliferation, said antisense oligonucleotide having SEQ ID NO: 3, wherein cellular proliferation is restenosis.

12. An antisense oligonucleotide for inhibiting cellular proliferation, said antisense oligonucleotide being complementary to a 3' untranslated region (3'-UTR) of cyclin E transcript for inhibiting the expression of cyclin E, thus inhibiting cellular proliferation, said antisense oligonucleotide having SEQ ID NO: 5, wherein cellular proliferation is restenosis.

13. An antisense oligonucleotide for inhibiting cellular proliferation, said antisense oligonucleotide being complementary to a 3' untranslated region (3'-UTR) of cyclin E transcript for inhibiting the expression of cyclin E, thus inhibiting cellular proliferation, said antisense oligonucleotide having SEQ ID NO: 6, wherein cellular proliferation is restenosis.

14. An antisense oligonucleotide for inhibiting cellular proliferation, said antisense oligonucleotide being complementary to a 3' untranslated region (3'-UTR) of cyclin E transcript for inhibiting the expression of cyclin E, thus inhibiting cellular proliferation, said antisense oligonucleotide having SEQ ID NO: 7, wherein cellular proliferation is restenosis.

15. An antisense oligonucleotide for inhibiting cellular proliferation, said antisense oligonucleotide being complementary to a 3' untranslated region (3'-UTR) of cyclin E transcript for inhibiting the expression of cyclin E, thus inhibiting cellular proliferation, said antisense oligonucleotide having SEQ ID NO: 8, wherein cellular proliferation is restenosis.

16. An antisense oligonucleotide for inhibiting cellular proliferation, said antisense oligonucleotide being complementary to a 3' untranslated region (3'-UTR) of cyclin E transcript for inhibiting the expression of cyclin E, thus inhibiting cellular proliferation, said antisense oligonucleotide having SEQ ID NO: 9, wherein cellular proliferation is restenosis.

17. An antisense oligonucleotide for inhibiting cellular proliferation, said antisense oligonucleotide being complementary to a 3' untranslated region (3'-UTR) of cyclin E transcript for inhibiting the expression of cyclin E, thus inhibiting cellular proliferation, said antisense oligonucleotide having SEQ ID NO: 10, wherein cellular proliferation is restenosis.

18. An antisense oligonucleotide for inhibiting cellular proliferation, said antisense oligonucleotide being complementary to a 3' untranslated region (3'-UTR) of cyclin E transcript for inhibiting the expression of cyclin E, thus inhibiting cellular proliferation, said antisense oligonucleotide having SEQ ID NO: 12, wherein cellular proliferation is restenosis.

19. An antisense oligonucleotide for inhibiting cellular proliferation, said antisense oligonucleotide being complementary to a 3' untranslated region (3'-UTR) of cyclin E transcript for inhibiting the expression of cyclin E, thus inhibiting cellular proliferation, said antisense oligonucleotide having SEQ ID NO: 13, wherein cellular proliferation is restenosis.

20. A pharmaceutical composition comprising an antisense oligonucleotide as defined in claim 11, and, in combination with a pharmaceutically acceptable carrier.

21. A method for preventing proliferation of tumor cells comprising the step of administering intravenously to a patient an antisense oligonucleotide complementary to a 5' untranslated region (5'-UTR) of cyclin E transcript for inhibiting the expression of cyclin E, thus inhibiting cellular proliferation of the tumor cells, said antisense oligonucleotide having SEQ ID NO: 3.

22. A method for preventing proliferation of tumor cells comprising the step of administering intravenously to a patient an antisense oligonucleotide complementary to a 3' untranslated region (3'-UTR) of cyclin E transcript for inhibiting the expression of cyclin E, thus inhibiting cellular proliferation of the tumor cells, said antisense oligonucleotide having SEQ ID NO: 5.

23. A method for preventing proliferation of tumor cells comprising the step of administering intravenously to a patient an antisense oligonucleotide complementary to a 3' untranslated region (3'-UTR) of cyclin E transcript for inhibiting the expression of cyclin E, thus inhibiting cellular proliferation of the tumor cells, said antisense oligonucleotide having SEQ ID NO: 6.

24. A method for preventing proliferation of tumor cells comprising the step of administering intravenously to a patient an antisense oligonucleotide complementary to a 3' untranslated region (3'-UTR) of cyclin E transcript for inhibiting the expression of cyclin E, thus inhibiting cellular proliferation of the tumor cells, said antisense oligonucleotide having SEQ ID NO: 7.

25. A method for preventing proliferation of tumor cells comprising the step of administering intravenously to a patient an antisense oligonucleotide complementary to a 3' untranslated region (3'-UTR) of cyclin E transcript for inhibiting the expression of cyclin E, thus inhibiting cellular proliferation of the tumor cells, said antisense oligonucleotide having SEQ ID NO: 8.

26. A method for preventing proliferation of tumor cells comprising the step of administering intravenously to a patient an antisense oligonucleotide complementary to a 3' untranslated region (3'-UTR) of cyclin E transcript for inhibiting the expression of cyclin E, thus inhibiting cellular proliferation of the tumor cells, said antisense oligonucleotide having SEQ ID NO: 9.

27. A method for preventing proliferation of tumor cells comprising the step of administering intravenously to a patient an antisense oligonucleotide complementary to a 3' untranslated region (3'-UTR) of cyclin E transcript for inhibiting the expression of cyclin E, thus inhibiting cellular proliferation of the tumor cells, said antisense oligonucleotide having SEQ ID NO: 10.

28. A method for preventing proliferation of tumor cells comprising the step of administering intravenously to a patient an antisense oligonucleotide complementary to a 3' untranslated region (3'-UTR) of cyclin E transcript for inhibiting the expression of cyclin E, thus inhibiting cellular proliferation of the tumor cells, said antisense oligonucleotide having SEQ ID NO: 12.

29. A method for preventing proliferation of tumor cells comprising the step of administering intravenously to a patient an antisense oligonucleotide complementary to a 3' untranslated region (3'-UTR) of cyclin E transcript for inhibiting the expression of cyclin E, thus inhibiting cellular proliferation of the tumor cells, said antisense oligonucleotide having SEQ ID NO: 13.

30. A method for preventing cellular proliferation, wherein the cellular proliferation is restenosis, comprising the step of administering to a patient at a site of dilatation of an artery of the patient an antisense oligonucleotide complementary to a 5' untranslated region (5'-UTR) of cyclin E transcript for inhibiting the expression of cyclin E, said antisense oligonucleotide having SEO ID NO: 3.

31. A method for preventing cellular proliferation, wherein the cellular proliferation is restenosis, comprising the step of administering to a patient at a site of dilatation of an artery of the patient an antisense oligonucleotide complementary to a 3' untranslated region (3'-UTR) of cyclin E transcript for inhibiting the expression of cyclin E, said antisense oligonucleotide having SEQ ID NO: 5.

32. A method for preventing cellular proliferation, wherein the cellular proliferation is restenosis, comprising the step of administering to a patient at a site of dilatation of an artery of the patient an antisense oligonucleotide complementary to a 3' untranslated region (3'-UTR) of cyclin E transcript for inhibiting the expression of cyclin E, said antisense oligonucleotide having SEQ ID NO: 6.

33. A method for preventing cellular proliferation, wherein the cellular proliferation is restenosis, comprising the step of administering to a patient at a site of dilatation of an artery of the patient an antisense oligonucleotide complementary to a 3' untranslated region (3'-UTR) of cyclin E transcript for inhibiting the expression of cyclin E, said antisense oligonucleotide having SEQ ID NO: 7.

34. A method for preventing cellular proliferation, wherein the cellular proliferation is restenosis, comprising the step of administering to a patient at a site of dilatation of an artery of the patient an antisense oligonucleotide complementary to a 3' untranslated region (3'-UTR) of cyclin E transcript for inhibiting the expression of cyclin E, said antisense oligonucleotide having SEQ ID NO: 8.

35. A method for preventing cellular proliferation, wherein the cellular proliferation is restenosis, comprising the step of administering to a patient at a site of dilatation of an artery of the patient an antisense oligonucleotide complementary to a 3' untranslated region (3'-UTR) of cyclin E transcript for inhibiting the expression of cyclin E, said antisense oligonucleotide having SEQ ID NO: 9.

36. A method for preventing cellular proliferation, wherein the cellular proliferation is restenosis, comprising the step of administering to a patient at a site of dilatation of an artery of the patient an antisense oligonucleotide complementary to a 3' untranslated region (3'-UTR) of cyclin E transcript for inhibiting the expression of cyclin E, said antisense oligonucleotide having SEQ ID NO: 10.

37. A method for preventing cellular proliferation, wherein the cellular proliferation is restenosis, comprising the step of administering to a patient at a site of dilatation of an artery of the patient an antisense oligonucleotide complementary to a 3' untranslated region (3'-UTR) of cyclin E transcript for inhibiting the expression of cyclin E, said antisense oligonucleotide having SEQ ID NO: 11.

38. A method for preventing cellular proliferation, wherein the cellular proliferation is restenosis, comprising the step of administering to a patient at a site of dilatation of an artery of the patient an antisense oligonucleotide complementary to a 3' untranslated region (3'-UTR) of cyclin E transcript for inhibiting the expression of cyclin E, said antisense oligonucleotide having SEQ ID NO: 12.

* * * * *